United States Patent [19]

Lesher et al.

[11] 3,992,380

[45] Nov. 16, 1976

[54] 5,8-DIHYDRO-5-OXO-2-(4-OR 3-PYRIDINYL)PYRIDO[2,3-D]PYRIMIDINE-6-CARBOXYLIC ACIDS AND ESTERS

[75] Inventors: George Y. Lesher, Rensselaer; Baldev Singh, East Greenbush, both of N.Y.

[73] Assignee: Sterling Drug Inc., New York, N.Y.

[22] Filed: Mar. 3, 1975

[21] Appl. No.: 555,051

[52] U.S. Cl. .................. 260/256.4 F; 260/256.4 C; 260/256.4 N; 424/251
[51] Int. Cl.$^2$ ...................................... C07D 487/04
[58] Field of Search ............................ 260/256.4 F

[56] References Cited
UNITED STATES PATENTS

| | | | |
|---|---|---|---|
| 3,673,184 | 6/1972 | Minami et al. | 260/256.4 F |
| 3,770,742 | 11/1973 | Matsumoto et al. | 260/256.4 F |
| 3,887,557 | 6/1975 | Minami et al. | 260/256.4 F |

FOREIGN PATENTS OR APPLICATIONS

| | | | |
|---|---|---|---|
| 1,129,358 | 10/1968 | United Kingdom | 260/256.4 F |

*Primary Examiner*—Nicholas S. Rizzo
*Assistant Examiner*—James H. Turnipseed
*Attorney, Agent, or Firm*—Robert K. Bair; B. Woodrow Wyatt

[57] ABSTRACT

Antibacterial 5,8-dihydro-8-(lower-alkyl)-5-oxo-2-Q-4-$R_2$-6-Z-pyrido[2,3-d]pyrimidine (I) where Z is carboxy or lower-carbalkoxy, $R_2$ is hydrogen or lower-alkyl and Q is 4(or 3)-pyridinyl or 4(or 3)-pyridinyl having one or two lower-alkyl substituents is prepared by heating di-(lower-alkyl) N-(2-Q-6-$R_2$-4-pyrimidinyl)aminomethylenemalonate (III) to produce 5,8-dihydro-5-oxo-2-Q-4-$R_2$-6-Z-pyrido[2,3-d]pyrimidine (II) which is tautomeric with 5-hydroxy-2-Q-4-$R_2$-6-Z-pyrido[2,3-d]pyrimidine (IIA) where Q and $R_2$ are the same as in I above and Z is lower-carbalkoxy, reacting II(or IIA) with a lower-alkylating agent to produce I where Z is lower-carbalkoxy and hydrolyzing this ester (I) to produce I where Z is carboxy. Alternatively, the acid (II or IIA where Z is COOH) can be alkylated after first hydrolyzing the ester (II or IIA where Z is lower-carbalkoxy). The preparations of the intermediate III and intermediates used in its preparation are given.

10 Claims, No Drawings

5,8-DIHYDRO-5-OXO-2-(4-OR 3-PYRIDINYL)PYRIDO[2,3-d]PYRIMIDINE-6-CARBOXYLIC ACIDS AND ESTERS

CROSS-REFERENCE TO RELATED APPLICATIONS

The instant application discloses as intermediates certain di-(lower-alkyl) N-(2-Q-6-$R_2$-4-pyrimidinyl)aminomethylenemalonates (III), their preparation and their intermediate 4-amino-2-Q-6-$R_2$-pyrimidines (IV), all of which are disclosed and claimed in copending U.S. application Ser. No. 555,067, filed Mar. 3, 1975.

BACKGROUND OF THE INVENTION

A. Field of the Invention

This invention relates to 5,8-dihydro-5-oxopyrido[2,3-d]pyrimidine-6-carboxylic acids useful as antibacterial agents, and to intermediates and processes for their preparation.

B. Description of the Prior Art

The Sterling Drug Inc. Lesher U.S. Pat. No. 3,320,257, issued May 16, 1967, discloses, inter alia, 2-$R_2$-4-$R_4$-5,8-dihyro-5-oxo-6-Z-8-R-pyrido[2,3-d]pyrimidines where $R_2$ and $R_4$ are each hydrogen, lower-alkyl, lower-alkoxy, lower-alkylamino, lower-alkylmercapto, phenylmethyl, phenyloxy, phenylamino or phenylmercapto, Z is carboxy or lower-carbalkoxy, and R is lower-alkyl. The compounds are shown to have antibacterial activity.

The Dainippon Pharmaceutical Co., Ltd. British patent specification No. 1,129,358, published Oct. 2, 1968, discloses as antibacterial agents the 5,8-dihydro-5-oxopyrido[2,3-d]pyrimidine derivatives having the formula 10/10

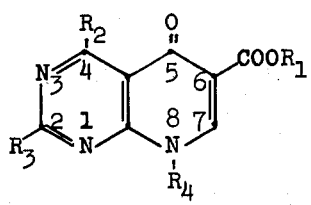

wherein $R_1$ stands for hydrogen or a lower alkyl radical, $R_2$ stands for hydrogen, a lower alkyl radical, a hydroxy group, a halogen atom, a lower alkoxy radical, an amino group or a lower alkylthio radical, $R_3$ stands for hydrogen, a lower alkyl radical, a hydroxy group, a lower alkoxy radical, a lower alkylthio group or a radical of formula

(in which R' stands for hydrogen, an alkyl radical, a cycloalkyl radical, an amino group, a hydroxyalkyl radical or an alkyl-substituted aminoalkyl radical, R'' stands for hydrogen or an alkyl radical or R' and R'', together with the nitrogen atom to which they are bonded, form a heterocyclic ring), and $R_4$ stands for hydrogen or an alkyl radical."

The R. Bellon Lab. German patent application No. DT 2,338,325, published Feb. 7, 1974, is abstracted as follows in the DERWENT "Central Patents Index Alerting Bulletin," Week V7, page B-7, Feb. 7, 1974: "8-Alkyl-5-oxo-5,8-dihydro-pyrido derivs of (2,3-d) pyrimidine 6-carboxylic acids - antibacterials. Cpds (I):

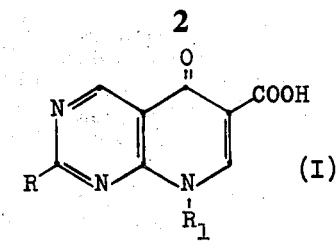

(where R is H, 1–5C alkoxy, 1–5C alkylthio or opt. substd. phenyl or $NR_1R_2$; $R_1$ and $R_2$ are 1–5C alkyl or a heterocyclic 5- or 6-membered ring opt. substd and opt. contg a further hetero-atom) are prepd by reacting 2-R-5-carbalkoxy-5-halo-pyrimidine with $R_1NHCH_2CH_2COOEt$, cyclising the product to give a 5-oxo-6-carbalkoxy-5,6,7,8-tetrahydro pyrido (2,3-d) pyrimidine, treating this with a halogenating agent, dehalogenating the halogenated product and hydrolysing the ester; when R is $NR_1R_2$ this gp. may be introduced before or after the halogenation stage. 1.8.73 as 338325 (clg. 2.8.72 - FR-027876) CO7d 57/20 (7.2.74) BELLON LAB, R."

SUMMARY OF THE INVENTION

In one composition aspect, the invention relates to certain 5,8-dihydro-8-$R_1$-5-oxo-2-Q-6-Z-pyrido[2,3-d]-pyrimidines (I) which are useful as antibacterial agents.

In another composition aspect, the invention relates to 5,8-dihydro-5-oxo-2-Q-4-$R_2$-6-Z-pyrido[2,3-d]pyrimidines (II) and their tautomeric 5-hydroxy-2-Q-4-$R_2$-6-Z-pyrido[2,3-d]pyrimidines (IIA) which are useful as intermediates in the preparation of the above final products.

The invention in a process aspect comprises heating a di-(lower-alkyl) N-(2-Q-6-$R_2$-4-pyrimidinyl)aminomethylene-malonate (III) to produce II(or IIA) where Z is a lower-carbalkoxy, reacting II(or IIA) where Z is a lower-carbalkoxy with a lower-alkylating agent to produce I where Z is lower-carbalkoxy and hydrolyzing I where Z is lower-carbalkoxy to produce I where Z is COOH. Other process aspects relate to: the said step of converting III to II(or IIA) where Z is lower-carbalkoxy; the two steps of alkylating II(or IIA) to product I where Z is lower-carbalkoxy and hydrolyzing the latter to product I where Z is carboxy; and, the alternative two-step conversion of hydrolyzing II(or IIA) where Z is lower-carbalkoxy to product II(or IIA) where Z is carboxy and alkylating II where Z is carboxy to produce I where Z is carboxy.

DETAILED DESCRIPTION INCLUSIVE OF PREFERRED EMBODIMENTS

The invention in a composition aspect resides in the class of compounds designated as 5,8-dihydro-8-(lower-alkyl)-5-oxo-2-Q-4-$R_2$-6-Z-pyrido[2,3-d]pyrimidine having the formula I

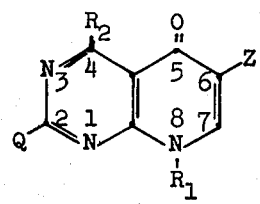

where $R_1$ is lower-alkyl, Z is carboxy or lower-carbalkoxy, $R_2$ is hydrogen or lower-alkyl and Q is 4(or 3)-pyridinyl or 4(or 3)-pyridinyl having one or two lower-alkyl substituents. The compounds of formula I possess the inherent applied use characteristics of having antibacterial properties, as determined by standard bacteriological evaluation procedures. A particularly preferred embodiment of this composition aspect of the invention is the compound of formula I where Q is 4-pyridinyl, $R_1$ is ethyl, $R_2$ is hydrogen and Z is COOH, that is, 8-ethyl-5,8-dihydro-5-oxo-2-(4-pyridinyl)-pyrido[2,3-d]pyrimidine-6-carboxylic acid.

The invention in another composition aspect resides in the class of compounds designated as 5,8-dihydro-5-oxo-2-Q-4-$R_2$-6-Z-pyrido[2,3-d]pyrimidine and its tautomeric 5-hydroxy-2-Q-4-$R_2$-6-Z-pyrido[2,3-d]pyrimidine having the respective formulas II and IIA

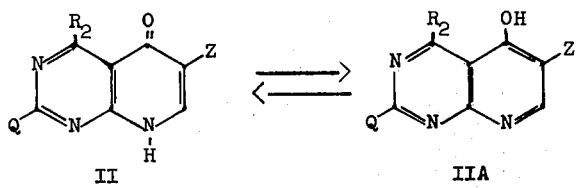

where Z, $R_2$ and Q have the meanings given hereinabove for formula I. A particularly preferred embodiment of this composition aspect of the invention is the compound of formula II or IIA where Q is 4-pyridinyl, $R_2$ is hydrogen and Z is carbethoxy, i.e., $COOC_2H_5$.

The invention in a process aspect comprises heating a di-(lower-alkyl) N-(2-Q-6-$R_2$-4-pyrimidinyl)aminomethylene-malonate having the formula III

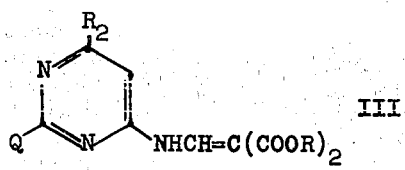

where $R_2$ and Q have the meanings given above for formula I and R is lower-alkyl, to product II(or IIA) where Z is COOR, reacting II(or IIA) where Z is COOR with a lower-alkylating agent to product I where Z is COOR and hydrolyzing I where Z is COOR to produce I where Z is COOH. Alternatively but less preferred, II(or IIA) where Z is COOR can be hydrolyzed to produce II(or IIA) where Z is COOH which can be reacted with a lower-alkylating agent to produce I where Z is COOH. The compounds of formula III and their preparation (discussed hereinbelow) are disclosed and claimed in copending U.S. application Ser. No. 555,067, filed Mar. 3, 1975.

The term "lower-alkyl" as used herein, e.g., for R or $R_1$ and as one of the meanings for $R_2$ or as a substituent for Q, means alkyl radicals having from one to six carbon atoms which can be arranged as straight or branched chains, illustrated by methyl, ethyl, n-propyl, isopropyl, n-butyl, sec.-butyl, tert.-butyl, isobutyl, n-amyl, n-hexyl, and the like.

The term "lower-carbalkoxy", as used herein, e.g., as one of the meanings for Z in formula I, II or IIA, means carbalkoxy radicals where the alkoxy portion can be straight- or branch-chained and has from one to six carbon atoms, as illustrated by carbomethoxy, carbethoxy, carbo-n-propoxy, carbisopropoxy, carbo-n-butoxy, carbo-tert.-butoxy and carbo-n-hexoxy.

Illustrative of the Q substituent in formulas I, II, IIA and III where Q is 4(or 3)-pyridinyl having one or two lower-alkyl substituents are the following [note that "pyridinyl" as used herein is the same as "pyridyl", the former now being the preferred term used in Chemical Abstracts]: 2-methyl-4-pyridinyl, 2,6-dimethyl-4-pyridinyl, 3-methyl-4-pyridinyl, 2-methyl-3-pyridinyl, 6-methyl-3-pyridinyl (preferably named 2-methyl-5-pyridinyl), 2,3-dimethyl-4-pyridinyl, 2,5-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-di-isopropyl-4-pyridinyl, 2,6-di-n-hexyl-4-pyridinyl, and the like. Because of ready availability, ease of preparation and/or high antibacterial activity of the final products, i.e., the 5,8-dihydro-8-(lower-alkyl)-5-oxo-2-[mono(or di)-(lower-alkyl)-4(or 3)-pyridinyl]-4-$R_2$-6-Z-pyrido[2,3-d]pyrimidines, preferred embodiments of this group are those where 4(or 3)-pyridinyl is substituted by one or two methyls, especially the 2-methyl-4-pyridinyl and 2,6-dimethyl-4-pyridinyl compounds. Other preferred embodients are those having unsubstituted-4(or 3)-pyridinyl as Q.

As shown above, 5,8-dihydro-5-oxo-2-Q-6-Z-pyrido[2,3-d]pyrimidine of formula II is tautomeric with 5-hydroxy-2-Q-6-Z-pyrido[2,3-d]-pyrimidine of formula IIA. As with all tautomeric systems, the rate of the transformation II ⇌ IIA and the ratio II/IIA are dependent on the thermodynamic environment, including the state of aggregation; so that measurements by any particular techniques do not necessarily have validity except under the conditions of the measurement, thereby, among other consequences, giving rise to problems for any simple designation of the physical embodiments. Thus, measurements of the infrared spectra, in potassium bromide admixture, or in chloroform or mineral oil, indicate existence predominantly as II and the names of the compounds herein therefore are preferably based on structure II, although it is understood that either or both structures are comprehended.

Also within the scope of the invention are the 6-carboxylic cationic salts of the above-described 5,8-dihydro-8-(lower-alkyl)-5-oxo-2-Q-pyrido[2,3-d]pyrimidine-6-carboxylic acids of formula I where Z is carboxy, i.e., COOH. Preferred types of salts are those having cations which do not increase the toxicity of the compound as a whole toward animal organisms. These comprise the alkali metal salts, e.g., the sodium or potassium salts; the lower-alkaline earth metal salts, e.g., magnesium or calcium salts; and, the ammonium or organic amine salts, e.g., diethanolamine or N-methyl-glucamine salts. Although medicinally acceptable salts are preferred, other and all cationic salts are within the scope of my invention. All such salts, including those having toxic cations, are useful in characterizing the free acids and as intermediates in purification of the free acids. The salts are prepared from the acids using conventional methods for converting acids into salts.

Also, the compounds of formula I are useful both in the free base form and in the form of acid-addition salts; and, both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, medicinally acceptable salts, that is, salts whose anions are relatively innocuous to the animal organism in medicinal doses of the salts, so that the beneficial antibacterial properties inherent in the free base are not vitiated by side effects ascribable to the anions. In practicing this invention, it is convenient to form the hydrochloride salts. However, other appropriate medicinally acceptable salts within the scope of the invention are those derived from mineral acids such as hydrobromic acid, hydriodic acid, nitric acid, phosphoric acid, sulfamic acid, and sulfuric acid; and organic acids such as acetic acid, citric acid, tartaric acid, lactic acid, methanesulfonic acid, ethanesulfonic acid, benzenesulfonic acid, p-toluenesulfonic acid, quinic acid, and the like, giving the hydrobromide, hydriodide, nitrate, phosphate, sulfamate, acetate, citrate, tartrate, lactate, methanesulfonate, ethanesulfonate, benzenesulfonate, p-toluenesulfonate and quinate, respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

Although medicinally acceptable salts of said basic compounds are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The molecular structures of the composition aspects (I, II, and IIA) of the invention were assigned on the basis of evidence provided by infrared, ultraviolet and nuclear magnetic resonance spectra, by chromatographic mobilities, and, by the correspondance of calculated and found values for the elementary anaylses for representative examples.

The manner of making and using the instant invention will now be generally described so as to enable a person skilled in the art of chemistry to make and use the same, as follows:

The preparation of the di-(lower-alkyl) N-(2-Q-6-R$_2$-4-pyrimidinyl)aminomethylenemalonate of formula III is carried out by reacting a 4-amino-2-Q-6-R$_2$-pyrimidine, where Q and R$_2$ have the meanings given above for Formula I, with a di-(lower-alkyl) (lower-alkoxy)-methylenemalonate. This reaction is carried out by heating said reactants, preferably in a molar ratio of 1:1 and preferably with stirring, either in the absence or presence of a suitable inert solvent, at about 100° to 200° C., preferably about 120° to 160° C. The reaction is conveniently run by heating the reactants, either in refluxing xylene or in the absence of a solvent at the said preferred heating temperature. Other suitable solvents inert under the reaction conditions include toluene, anisole, nitrobenzene, chlorobenzene, dimethylformamide, dimethylacetamide, tetramethylurea, pyridine, α-picoline, β-picoline, γ-picoline and the like. Alternatively, the above reaction can be carried out by preparing the di-(lower-alkyl) (lower-alkoxy)methylenemalonate of formula IV

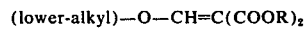  IV in situ without its actual isolation by heating a mixture of equimolar quantities of a 4-amino-2-Q-6-R$_2$-pyrimidine, a tri-(lower-alkyl) orthoformate, preferably the triethyl ester and a malonic ester of formula V, $CH_2(COOR)_2$, under the reaction conditions discussed above. Preferably, the reaction is run in the presence of a catalytic amount of an acidic catalyst, e.g., a strong inorganic acid such as hydrochloric acid, sulfuric acid, hydrobromic acid, phosphoric acid, and the like; an organic sulfonic acid such as p-toluenesulfonic acid, benzenesulfonic acid, methanesulfonic acid, ethanesulfonic acid, and the like; a Lewis acid such as zinc chloride, boron trichloride, boron tribromide, aluminum trichloride; other strong organic acids, e.g., trifluoroacetic acid, and the like.

The intermediate 4-amino-2-Q-6-R$_2$-pyrimidines are prepared by various procedures which are described generally in the following paragraphs and are further illustrated hereinbelow in the specific exemplary disclosure.

The preparation of 4-amino-2-Q-pyrimidines (where R$_2$ is hydrogen) is conveniently carried out by heating a pyridinecarboxamidine of the formula, Q—C(=NH)NH$_2$, with a β-(lower-alkoxy)-acrylonitrile, preferably β-ethoxyacrylonitrile to produce the 4 amino-2-Q-pyrimidine.

The preparation of 4-amino-2-Q-6-R$_2$-pyrimidines where R$_2$ is lower-alkyl are readily produced by reacting a pyridinecarboxamidine of the formula, Q—C(=NH)NH$_2$, with a lower-alkyl β-oxoalkanoate of the formula, R$_2$–COCH$_2$—COO—(lower-alkyl) to produce 2-Q-6-R$_2$-4-pyrimidinol, reacting the 4-pyrimidinol with a halogentating agent to produce 4-halo-2-Q-6-R$_2$-pyrimidine, reacting the 4-halo compound with hydrazine to produce 4-hydrazino-2-Q-6-R$_2$-pyrimidine and catalytically hydrogenating the 4hydrazino compound in the presence of a suitable catalyst, e.g., Raney nickel, to product 4-amino-2-Q-6-R$_2$-pyrimidine where R$_2$ is lower-alkyl.

The intermediate pyridinecarboxamidines of the formula, Q—C(=NH)NH$_2$, are generally known as compounds which are prepared by conventional methods.

The reaction of di-(lower-alkyl) N-(2-Q-6-R$_2$-4-pyrimidinyl)methylenemalonate (III) to produce a lower-alkyl 5,8-dihydro-5-oxo-2-Q-pyrido[2,3-d]pyrimidine-6-carboxylate (II where Z is lower-carbalkoxy) is carried out by heating III in an inert solvent at about 200°–325° C., preferably at about 250°–300° C. Such solvents include mineral oil, diethyl phthalate, dibenzyl ether, the eutectic mixture of diphenyl and diphenyl ether (Dowtherm A), and the like.

The reaction of 5,8-dihydro-5-oxo-2-Q-6-Z-pyrido[2,3-d]-pyrimidine (II) or its tautomeric 5-hydroxy-2-Q-6-Z-pyrido[2,3-d]pyrimidine (IIA) with a lower-alkylating agent to produce 5,8-dihydro-8-(lower-alkyl)-5-oxo-2-Q-6Z-pyrido[2,3-d]pyrimidine (I) is generally carried out by reacting said compound of formula II or IIA with a lower-alkyl ester of a strong inorganic acid or an organic sulfonic acid, said ester having the formula R$_1$-An, where An is an anion of a strong inorganic acid or an organic sulfonic acid, e.g., chloride, bromide, iodide, sulfate, methanesulfonate, benzenesulfonate, and para-toluenesulfonate, and R$_1$ is lower-alkyl. This alkylation is preferably run using a slight excess of the alkylating agent. The chloride, bromide, iodide or sulfate is preferred because of their ready availability; and the reaction is carried out preferably in the presence of an acid-acceptor. The acid-acceptor is a basic substance which preferably forms freely water-soluble by-products easily separable from the product of the reaction, including for example, sodium hydroxide, potassium hydroxide, sodium carbonate, potassium carbonate, sodium alkoxides, potassium alkoxides, sodium amide, and the like. The acid-acceptor takes up the hydrogen halide (or HAn) which is split out during the course of the reaction and also takes up the proton from the 1 position of II or from the 4-OH of IIA to generate the resulting anion of II or IIA. The reaction can be carried out in either the presence or absence of a suitable solvent, but preferably in a solvent such as lower-alkanol, acetone, dioxane, dimethyformamide, dimethyl sulfoxide, hexamethylphosphoramide, or a mixture of solvents, e.g., a mixture of water and a lower-alkanol. The reaction is generally carried out at a temperature between about room temperature (about 20°–25° C.) and 150° C., preferably heating the lower-alkyl ester (II or IIA where Z is lower-carbalkoxy) on a steam bath in a stirred mixture of dimethylformamide and anhydrous potassium carbonate. To obtain the final product in acid form, the lower-alkyl ester is readily hydrolyzed by heating it with aqueous potassium or sodium hydroxide solution to obtain the compound of formula I where Z is COOH. Alternatively, but with lower-yields, the 5,8-dihydro-5-oxo-2-Q-pyrido[2,3-d]pyrimidine-6-carboxylic acid can be alkylated directly as described above preferably using an aqueous lower-alkanol, e.g., ethanol, as the solvent and an acid-acceptor, e.g., potassium carbonate; in this alkylation of the 6-carboxylic acid, at least two molar equivalents of $R_1$-An is needed since some ester formation of the 6-carboxy group occurs.

The 5,8-dihydro-8-(lower-alkyl)-5-oxo-2-Q-4-$R_2$-6-Z-pyrido[2,3-d]pyrimidine-6-carboxylic acids of the invention, that is, the compounds of formula I where Z is carboxy and Q is as defined in formula I, when tested according to standard in vitro bacteriological evaluation procedures possess antibacterial activity, for example, against organisms such as *Klebsiella pneumoniae*, *Escherichia coli* and *Proteus vulgaris*, at concentrations in the range of about 5 to 65 mcg. per ml. Also, said compounds of our invention when tested according to standard in vivo bacteriological evaluation procedures in mice were found to have significant activity against bacteria, for example, *Escherichia coli* when administered orally at a dose level in the range of about 50 to 200 mg./kg. (single dose administered 30 minutes after infection and mice observed for 7 days).

The following examples will further illustrate the invention without, however, limiting it thereto.

A. 4-AMINO-2-(PYRIDINYL)PYRIMIDINES AND INTERMEDIATES

A-1. 4-Amino-2-(4-pyridinyl)pyrimidine — To an ice cold and stirred solution of 172 g. of sodium methoxide in 800 ml. of methanol was slowly added 304 g. of isonicotinamidine dihydrochloride; the resulting mixture was stirred for fifteen minutes and filtered. The inorganic residue was washed with methanol and the filtrate plus washings were evaporated to dryness in vacuo on a steam bath to yield 288 g. of isonicotinamidine in free base form. A mixture of said isonicotinamidine and 150 g. of β-ethoxyacrylonitrile was heated in an oil bath at 130°–150° C. for about 4 hours. After removal of the ethanol (formed by the reaction) by heating in vacuo on a steam bath, the remaining material was dissolved in 200 ml. of concentrated hydrochloric acid and 100 ml. of water, and the solution allowed to stand overnight at room temperature (about 20°–25° C.). The solution was treated with decolorizing charcoal, heated on a steam bath for thirty minutes, filtered and the filtrate basified with ammonium hydroxide. The resulting solid was collected, washed with cold water, air-dried, digested with hot methanol, separated and air-dried to yield, as a tan powder, 105 g. of 4-amino-2-(4-pyridinyl)pyrimidine, m.p. 260°–262° C.

The hydrochloride salt of 4-amino-2-(4-pyridinyl)-pyrimidine was prepared as follows: a mixture containing 10 g. of 4-amino-2-(4-pyridinyl)pyrimidine, 30 ml. of water and 20 ml. of concentrated hydrochloric acid was warmed to effect solution. To the warm solution was added isopropyl alcohol to turbidity (about 110 ml) whereupon crystals started to separate. The mixture was cooled and the crystallized precipitate was collected, washed with isopropyl alcohol and ether and dried in vacuo at 80° C. to yield 9.5 of 4-amino-2-(4-pyridinyl)pyrimidine dihydrochloride as its monohydrate, m.p. 229° C. with decomposition.

A-2. 4-Amino-2-(3-pyridinyl)pyrimidne, m.p. 157°–159° C., 45 g., was prepared following the procedure described in Ex. A-1 using 72 g. of nicotinamide dihydrochloride, 54 g. of sodium methoxide, 400 ml. of methanol, 60 g. of beta-ethoxyacrylonitrile and a heating period of 3 hours at 100°–125° C.

A-3. 6-Methyl-2-(4-pyridinyl)-4-pyrimidinol — A mixture containing 15.8 g. of isonicotinamidine hydrochloride, 16.8 g. of sodium methoxide, 17 g. of ethyl acetoacetate and 100 ml. of ethanol was refluxed with stirring for seven hours and then evaporated to dryness. The residue was dissolved in water and the aqueous solution made acidic with acetic acid. The resulting solution was collected, washed with water, dried and recrystallized from ethanol to yield 6.7 g. of 6-methyl-2-(4-pyridinyl)-4-pyrimidinol, m.p. 236°–238° C.

A-4. 6-n-Propyl-2-(4-pyridinyl)-4-pyrimidinol — To an ice cooled solution containing 500 ml. of methanol and 16 g. of sodium methoxide was added 47.4 g. of isonicotinamidine hydrochloride; the mixture was stirred for 15 minutes and filtered to remove the precipitated sodium chloride; the filtrate was concentrated in vacuo; 56 g. of ethyl n-butylacetate was added; and the resulting mixture was heated in an oil bath at 160°–180° C. for 3 hours. After the reaction mixture had been cooled, the separated product was collected and recrystallized from ethanol to yield 38.9 g. of 6-n-propyl-2-(4-pyridinyl)-4-pyrimidinol, m.p. 173°–174° C.

A-5. 4-Chloro-6-methyl-2-(4-pyridinyl)pyrimidine — A mixture containing 26.5 g. of 6-methyl-2-(4-pyridinyl)-4-pyrimidinol, 27 g. of phenylphosphonic dichloride and 75 ml. of phosphorus oxychloride was refluxed for 4 hours and then poured onto ice. The resulting aqueous mixture was made basic with ammonium hydroxide. The product was extracted from the alkaline mixture using chloroform and the chloroform extract was concentrated in vacuo. The residue was filtered through a silica gel column using ether as the solvent and eluent. Removal of the ether yielded 12.9 g. of 4-chloro-6-methyl-2-(4-pyridinyl)pyrimidine, m.p. 128°–130° C.

A-6. 4-Hydrazino-6-methyl-2-(4-pyridinyl)pyrimidine — A solution containing 36 g. of 4-chloro-6-methyl-2-(4-pyridinyl)-pyrimidine, 100 ml. of ethanol and 20 ml. of hydrazine hydrate was refluxed on a steam bath for 2 hours and then evaporated to dryness. The residue was partitioned between water and chloroform. The chloroform layer was separated and the chloroform distilled off in vacuo to yield, as a yellow solid, 31.2 g. of 4-hydrazino-6-methyl-2-(4-pyridinyl)pyrimidine, m.p. 150°–152° C., which was used in the following step given in Example A-7. A 3.6 g. portion of this hydrazine was converted into its dicyclohexylsulfamate salt which was recrystallized from ethanol to yield 7.2 g. of said salt, m.p. <280° C. with decomposition.

A-7. 4-Amino-6-methyl-2-(4-pyridinyl)pyrimidine — A mixture containing 31 g. of 4-hydrazino-6-methyl-2-(4-pyridinyl)pyrimidine, 150 ml. of ethanol and 2 g. of Raney nickel was shaken under hydrogen (48 psi) and heated to 63°C. whereupon there was an uptake of 10.7 lbs. of hydrogen. The reaction mixture was cooled to room temperature and the catalyst was filtered off. The filtrate was concentrated in vacuo to yield an orange solid that was crystallized from isopropyl alcohol to yield, as tan crystals, 22.6 g. of 4-amino-6-methyl-2-(4pyridinyl)pyrimidine, m.p. 192°–194° C.

Following the procedure described in Example A-1 but using in place of isonicotinamidine a molar equivalent quantity of the appropriate pyridinecarboxamidine, i.e., Q—C(=NH)NH$_2$, the 4-amino-2-Q-pyrimidines of Examples A-8 through A-12 are obtained:

A-8. 4-Amino-2-(2-methyl-4-pyridinyl)pyrimidine using 2-methylisonicotinamidine.

A-9. 4-Amino-2-(3-methyl-4-pyridinyl)pyrimidine using 3-methylisonicotinamidine.

A-10. 4-Amino-2-(2-ethyl-4-pyridinyl)pyrimidine using 2-ethylisonicotinamidine.

A-11. 4-Amino-2-(2,6-dimethyl-4-pyridinyl)pyrimidine using 2,6-dimethylisonicotinamidine.

A-12. 4-Amino-6-n-propyl-2-(4-pyridinyl)pyrimidine is obtained in three steps following the respective procedures of Examples A-5, A-6 and A-7 starting with a molar equivalent quantity of 6-n-propyl-2-(4-pyridinyl)-4-pyrimidinol in place of 6-methyl-2-(4-pyridinyl)-4-pyrimidinol to obtain successively 4-chloro-6n-propyl-2-(4-pyridinyl)pyrimidine, 4-hydrazino-6-n-propyl-2-(4-pyridinyl)pyrimidine and then said 4-amino-6-n-propyl-2-(4-pyridinyl)pyrimidine.

B. DI-(LOWER-ALKYL [2-(PYRIDINYL)-4-PYRIMIDINYL]-AMINOMETHYLENEMALONATES

B-1. Diethyl N-[2-(4-pyridinyl)-4-pyrimidinyl]-aminomethylenemalonate — A mixture containing 108 g. of 4-amino-2-(4-pyridinyl)pyrimidine, 180 g. of diethyl ethoxymethylenemalonate and 300 ml. of xylene was heated with stirring in an oil bath at 190°–195° C. for 72 hours, while allowing the ethanol (formed by the reaction) and xylene solvent to evaporate by using an air cooled condenser. The oily residue was treated with 500 ml. of ethanol followed by decolorizing charcoal. The mixture was filtered and the filtrate evaporated to dryness in vacuo. The residue was crystallized from ethanol-ether to give 130 g. of diethyl N-[2-(4-pyridinyl)-4-pyrimidinyl]aminomethylenemalonate, m.p. 138°–140° C. This compound was also prepared in the absence of a solvent as follows: a mixture containing 100 g. of 2-amino-4-(4-pyridinyl)pyrimidine and 190 g. of diethyl ethoxyaminomethylenemalonate was heated with stirring for 20 hours at 135°–143° C. and was then allowed to cool slowly. Crystallization started when the temperature was above 80° C. whereupon 100 ml. of absolute ethanol was added. The mixture was then allowed to cool to room temperature and the crystalline precipitate was collected, washed with cold ethanol and then ether. The resulting tan crystalline material was recrystallized from 400 ml. of absolute ethanol using decolorizing charcoal to yield, as yellow crystals, 105 g. of diethyl N-[2-(4-pyridinyl)-4-pyrimidinyl]aminomethylenemalonate, m.p. 143°–145° C. A 45 g. portion of this compound was dissolved in 225 ml. of isopropyl alcohol, treated with decolorizing charcoal and filtered. To the filtrate was added one equivalent of concentrated hydrochloric acid whereupon the crystallized hydrochloride separated immediately. The mixture was cooled and the product was collected, washed successively with cold isopropyl alcohol and ether, and dried in vacuo at 80° C. to yield 48 g. of diethyl N-[2-(4-pyridinyl)-4-pyrimidinyl]aminomethylenemalonate hydrochloride, m.p. 227°–230° C. with decomposition.

B-2. Diethyl N-[2-(3-pyridinyl)-4-pyrimidinyl)aminomethylenemalonate — A mixture containing 44 g. of 4-amino-2-(3-pyridinyl)pyrimidine and 55 g. of diethyl ethoxymethylenemalonate was heated in an oil bath at 160°–170° C. for 3 hours and then cooled to room temperature. The reaction mixture was dissolved in methylene dichloride and the solution filtered through a column of silica gel followed by elution of the column with 10% methanol in ether. Evaporation of the eluate yielded a yellow solid which was recrystallized from ether-isopropyl alcohol to yield 45 g. of diethyl N-[2-(3-pyridinyl)-4-pyrimidinyl]aminomethylenemalonate, m.p. 115°–117° C.

B-2. Dimethyl N-[2-(4-pyridinyl)-4-pyrimidinyl]aminomethylenemalonate — A mixture containing 10 g. of 4-amino-2-(4-pyridinyl)pyrimidine, 10 g. of dimethyl methoxymethylenemalonate and 750 ml. of xylene was refluxed with stirring for 14 hours and then filtered to remove any insoluble reddish residue. The solution was evaporated to dryness; the residue was dissolved in 400 ml. of 50-50 mixture (v/v) of methanol-chloroform; and, the solution was treated with decolorizing charcoal and filtered. The filtrate was concentrated to a volume of about 200 ml. and was allowed to cool. The resulting yellow precipitate was collected, washed with methanol and dried in vacuo at 80° C. to give 14.2 g. of dimethyl N-[2-(4-pyridinyl)-4-pyrimidinyl]aminomethylenemalonate, m.p. 209°–211° C.

B-4. Dimethyl N-[2-(3-pyridinyl)-4-pyrimidinyl]aminomethylenemalonate — A mixture containing 8.6 g. of 4-amino-2-(3-pyridinyl)pyrimidine and 15 g. of dimethyl ethoxymethylenemalonate was heated in an oil bath at 140°–150° C. for 4 hours. The reaction mixture was then dried in vacuo and the remaining oily residue was dissolved in methanol. The methanol solution was treated with decolorizing charcoal and filtered. The filtrate was chilled and the separated solid was collected and dried in vacuo at 80° C. to yield 11.8 g. of dimethyl N-[2-(3-pyridinyl)-;b 4-pyrimidinyl]aminomethylenemalonate, m.p. 183°–184° C.

B-5. Diethyl N-[6-methyl-2-(4-pyridinyl)-4-pyrimidinyl]aminomethylenemalonate — A mixture containing 15.2 g. of 4-amino-6-methyl-2-(4-pyridinyl)pyrimidine and 25 ml. of diethyl ethoxymethylenemalonate was heated with stirring at 150°–160° C for 2 hours and then allowed to cool. The separated product was collected and crystallized from methanol to yield 22.6 g. of diethyl N-[6-methyl-2-(4-pyridinyl)-

4-pyrimidinyl]aminomethylenemalonate, m.p. 169°–171° C.

Following the procedure described above in Example B-1 but using in place of diethyl ethoxymethylenemalonate a molar equivalent quantity of the appropriate di-(lower-alkyl) (lower-alkoxy)methylenemalonate, the compounds of Examples B-6 through B-10 are obtained:

B-6. Di-n-propyl N-[2-(4-pyridinyl)-4-pyrimidinyl]aminomethylenemalonate using di-n-propyl n-propoxymethylenemalonate.

B-7. Diisopropyl N-[2-(4-pyridinyl)-4-pyrimidinyl]aminomethylenemalonate using diisopropyl isopropoxymethylenemalonate.

B-8. Di-n-butyl N-[2-(4-pyridinyl)-4-pyrimidinyl]aminomethylenemalonate using di-n-butyl n-butoxymethylenemalonate.

B-9. Diisobutyl N-[2-(4-pyridinyl)-4-pyrimidinyl]aminomethylenemalonate using diisobutyl ethoxymethylenemalonate.

B-10. Di-n-hexyl N-[2-(4-pyridinyl)-4-pyrimidinyl]aminomethylenemalonate using di-n-hexyl n-hexoxymethylenemalonate.

Following the procedures described in Example B-1 but using in place of 4-amino-2-(4-pyridinyl)pyrimidine a molor equivalent quantity of the appropriate 4-amino-2-Q-pyrimidine, the compounds of Examples B-11 through B-15 are obtained:

B-11. Diethyl N-[2-(2-methyl-4-pyrimidinyl)-4-pyrimidinyl]aminomethylenemalonate using 4-amino-2-(2-methyl-4-pyridinyl)pyrimidine.

B-12. Diethyl N-[2-(3-methyl-4-pyridinyl)-4-pyrimidinyl]aminomethylenemalonate using 4-amino-2-(3-methyl-4-pyridinyl)pyrimidine.

B-13. Diethyl N-[2-(2-ethyl-4-pyridinyl)-4-pyrimidinyl]aminomethylenemalonate using 4-amino-2-(2-ethyl-4-pyridinyl)pyrimidine.

B-14. Diethyl N-[2-(2,6-dimethyl-4-pyridinyl)-4-pyrimidinyl]aminomethylenemalonate using 4-amino-2-(2,6-dimethyl-4-pyridinyl)-pyrimidine.

B-15. Diethyl N-[6-n-propyl-2-(4-pyridinyl)-4-pyrimidinyl]aminomethylenemalonate is obtained following the procedure described in Example B-5 but using a molar equivalent quantity of 4-amino-6-n-propyl-2-(4-pyridinyl)pyrimidine in place of 4-amino-6-methyl-2-(4-pyridinyl)pyrimidine.

C. LOWER-ALKYL 5,8-DIHYDRO-5-OXO-2-(PYRIDINYL)-PYRIDO[2,3-d]PYRIMIDINE-6-CARBOXYLATES

C-1. Ethyl 5,8-dihydro-5-oxo-2-(4-pyridinyl)-pyrido[2,3-d]pyrimidine-6-carboxylate — To 1200 ml. of boiling and vigourously stirred Dowtherm A (eutectic mixture of diphenyl and diphenyl ether) was added over a period of about 2 minutes 110 g. of diethyl N-[2-(4-pyridinyl)-4-pyrimidinyl]aminomethylenemalonate and the resulting mixture was heated for 20 minutes and the solid (25 g.) that separated was collected. The filtrate was boiled (at 245°–250° C. for another 30 minutes and cooled. The separated solid (12 g.) was collected. The 25 g. and 12 g. fractions were crystallized separately from dimethylformamide, combined and recrystallized from dimethylformamide to yield 22 g. of ethyl 5,8-dihydro-5-oxo-2-(4-pyridinyl)-pyrido[2,3-d]-pyrimidine-6-carboxylate, m.p. 278°–280° C. This ethyl ester is converted into its corresponding 5,8-dihydro-5-oxo-2-(4-pyridinyl)-pyrido[2,3-d]pyrimidine-6-carboxylic acid by following the hydrolysis procedure given hereinbelow in Example D-2 and using corresponding molar equivalent quantities of the ester and sodium hydroxide in aqueous methanol solution.

Corresponding lower-alkyl 5,8-dihydro-5-oxo-2-(4-pyridinyl)pyrido[2,3-d]pyrimidine-6-carboxylates are produced following the above-described procedure of Example C-1 but using in place of diethyl N-[2-(4-pyridinyl)-4-pyrimidinyl]aminomethylenemalonate a molar equivalent quantity of other di-(lower-alkyl) esters, e.g., dimethyl, di-n-propyl, diisopropyl, di-n-butyl, diisobutyl or di-n-hexyl N-[2-(4-pyridinyl)-4-pyrimidinyl]aminomethylenemalonate thereby yielding, respectively, methyl, n-propyl, isopropyl, n-butyl, isobutyl or n-hexyl 5,8-dihydro-5-oxo-2-(4-pyridinyl)-pyrido[2,3-d]pyridimine-6-carboxylate.

C-2. Ethyl-5,8-dihydro-5-oxo-2-(3-pyridinyl)-pyrido[2,3-d]pyrimidine-6-carboxylate, 29 g., m.p. 280°–282° C., was prepared following the procedure described in Example C-1 using 64 g. of diethyl N-[2-(3-pyridinyl)-4-pyrimidinyl]aminomethylenemalonate, 1300 ml. of Dowtherm A, a heating period of 90 minutes and recrystallization from dimethylformamide. This ethyl ester is converted into its corresponding 5,8-dihydro-5-oxo-2(3-pyridinyl)pyrido[2,3-d]pyrimidine-6-carboxylic acid by following the hydrolysis procedure given in Example D-2 and using corresponding molar equivalent quantities of the ester and sodium hydroxide in aqueous methanol solution.

Following the procedure described in Example C-1 but using in place of diethyl N-[2-(4-pyridinyl)-4-pyrimidinyl]aminomethylenemalonate a molar equivalent quantity of the appropriate diethyl N-[2-Q-6-$R_2$-4-pyridinyl]aminomethylenemalonate, the compounds of Examples C-3 through C-8 are obtained:

C-3. Ethyl 5,8-dihydro-2-(2-methyl-4-pyridinyl)-5-oxopyrido[2,3-d]pyrimidine-6-carboxylate using diethyl N-[2-(2-methyl-4-pyridinyl)-4-pyrimidinyl]aminomethylenemalonate.

C-4. Ethyl 5,8-dihydro-2-(3-methyl-4-pyridinyl)-5-oxopyrido[2,3-d]pyrimidine-6-carboxylate using diethyl N-[2-(3-methyl-4-pyridinyl)-4-primidinyl]aminomethylenemalonate.

C-5. Ethyl 2-(2-ethyl-4-pyridinyl)-5,8-dihydro-5-oxopyrido[2,3-d]pyrimidine-6-carboxylate using diethyl N-[2-(2-ethyl-4-pyridinyl)-4-pyrimidinyl]aminomethylenemalonate.

C-6. Ethyl 5,8-dihydro-2-(2,6-dimethyl-4-pyridinyl)-5-oxopyrido[2,3-d]pyrimidine-6-carboxylate using diethyl N-[2-(2,6-dimethyl-4-pyridinyl)-4-pyrimidinyl]aminomethylenemalonate.

C-7. Ethyl 5,8-dihydro-4-methyl-5-oxo-2-(4-pyridinyl)pyrido[2,3-d]pyrimidine-6-carboxylate using diethyl N-[6-methyl-2-(4-pyridinyl)-4-pyrimidinyl aminomethylenemalonate.

C-8. Ethyl 5,8-dihydro-5-oxo-4-n-propyl-2-(4-pyridinyl)pyrido[2,3-d]pyrimidine-6-carboxylate using diethyl N-[6-n-propyl-2-(4-pyridinyl)-4-pyrimidinyl]aminomethylenemalonate.

D. LOWER-ALKYL 5,8-DIHYDRO-8-(LOWER-ALKYL)-5-OXO-2-(PYRIDINYL)PYRIDO[2,3-d]PYRIMIDINE-6-CARBOXYLATES AND CORRESPONDING 6-CARBOXYLIC ACIDS

D-1. Ethyl 8-ethyl-5,8-dihydro-5-oxo-2-(4-pyridinyl)pyrido[2,3-d]pyrimidine-6-carboxylate A slurry of 19 g. of ethyl 5,8-dihydro-5-oxo-2-(4- pyridinyl)pyrido[2,3-d]pyrimidine-6-carboxylate, 16.8 g. of anhydrous potassium carbonate and 250 ml. of dimethylformamide was heated on a steam bath with stirring for 45 minutes; 6.5 ml. of ethyl iodide was added; and, the resulting reaction mixture was heated on a steam bath with stirring for 30 minutes. The dimethylformamide solvent was distilled off in vacuo and the residue was partitioned between water and chloroform. The chloroform solution was separated, treated with decolorizing charcoal and filtered, and then heated in vacuo to remove the chloroform. The residue was crystallized from methanolisopropyl alcohol to give, as yellow needles, 14.5 g. of ethyl 8-ethyl-5,8-dihydro-5-oxo-2-(4-pyridinyl)pyrido[2,3-d]pyrimidine-6-carboxylate.

Following the procedure described in Example D-1 but using molar equivalent quantities of the appropriate corresponding lower-alkyl 5,8-dihydro-5-oxo-2-(4-pyridinyl)pyrido[2,3-d]pyrimidine-6-carboxylate in place of the ethyl ester, there is obtained methyl, n-propyl, isopropyl, n-butyl, isobutyl, or n-hexyl 8-ethyl-5,8-dihydro-5-oxo-2-(4-pyridinyl)pyrido[2,3-d]pyrimidine-6-carboxylate. These lower-alkyl esters are converted to their corresponding 6-carboxylic acids following the hydrolysis procedure given below in Example D-2 using a corresponding molar equivalent quantity of the appropriate lower-alkyl ester.

D-2. 8-Ethyl-5,8-dihydro-5-oxo-2-(4-pyridinyl)pyrido[2,3-d]pyrimidine-6-carboxylic acid — A mixture containing 14 g. of ethyl 8-ethyl-5,8-dihydro-5-oxo-2-(4-pyridinyl)pyrido[2,3-d]pyrimidine-6-carboxylate, 20 ml. of 35% aqueous sodium hydroxide solution, 60 ml. of water and 80 ml. of methanol was heated with stirring on a steam bath for one hour. The methanol was distilled off in vacuo and the remaining mixture was filtered. The filtrate was acidified with hydrochloric acid and the resulting precipitate was collected, washed with water and crystallized from dimethylformamide to yield 12.5 g. of 8-ethyl-5,8-dihydro-5-oxo-2-(4-pyridinyl)pyrido[2,3-d]pyrimidine-6-carboxylic acid, m.p. 275°–277° C.

D-3. Ethyl 5,8-dihydro-8-ethyl-5-oxo-2-(3-pyridinyl)pyrido[2,3-d]pyrimidine-6-carboxylate, m.p. 194°–196° C., 14 g., was prepared following the procedure described in Example D-1 using 10 g. of ethyl 5,6-dihydro-5-oxo-2-(3-pyridinyl)pyrido[2,3-d]pyrimidinyl-6-carboxylate, 8.4 g. of anhydrous potassium carbonate. 125 ml. of dimethylformamide, 3.6 ml. of ethyl iodide, a heating period of forty-five minutes and purified as follows. The crude solid product obtained in this run was combined with 4.8 g. and 7 g. portions of the same crude product obtained in other runs and the combined solid was crystallized from methanol to yield, as tan crystals, said 14 g. of the product.

D-4. 5,8-Dihydro-8-ethyl-5-oxo-2-(3-pyridinyl)pyrido[2,3-d]pyrimidine-6-carboxylic acid, m.p. 278°–280° C., 10 g., was prepared following the procedure described in Example D-2 using 13 g. of ethyl 5,8-dihydro-8-ethyl-5-oxo-2-(3-pyridinyl)pyrido[2,3-d]pyrimidine-6-carboxylate, 100 ml. of 2N aqueous potassium hydroxide solution and drying the product in vacuo at 80° C.

Following the procedure described in Example D-1 but using in place of ethyl 5,8-dihydro-5-oxo-2-(4-pyridinyl)pyrido[2,3-d]pyrimidine-6-carboxylate a molar equivalent quantity of the appropriate lower-alkyl 5,8-dihydro-5-oxo-2-Q-pyrido[2,3-d]pyrimidine-6-carboxylate, the compounds of Examples D-5 through D-9 are obtained:

D-5. Ethyl 8-ethyl-5,8-dihydro-2-(2-methyl-4-pyridinyl)-5-oxopyrido[2,3-d]pyrimidine-6-carboxylate using ethyl 5,8-dihydro-2-(2-methyl-4-pyridinyl)-5-oxopyrido-[2,3-d]pyrimidine-6-carboxylate.

D-6. Ethyl 8-ethyl-5,8-dihydro-2-(3-methyl-4-pyridinyl)-5-oxopyrido[2,3-d]pyrimidine-6-carboxylate using ethyl 5,8-dihydro-2-(3-methyl-4-pyridinyl)-5-oxopyrido[2,3-d]pyrimidine-6-carboxylate.

D-7. Ethyl 8-ethyl-2-(2-ethyl-4-pyridinyl)-5,8-dihydro-5-oxopyrido[2,3-d]pyrimidine-6-carboxylate using ethyl 2-(2-ethyl-4-pyridinyl)-5,8-dihydro-5-oxopyrido[2,3-d]-pyrimidine-6-carboxylate.

D-8. Ethyl 8-ethyl-5,8-dihydro-2-(2,6-dimethyl-4-pyridinyl)-5-oxopyrido[2,3-d]pyrimidine-6-carboxylate using ethyl 5,8-dihydro-2-(2,6-dimethyl-4-pyridinyl)-5-oxopyrido-[2,3-d]pyrimidine-6-carboxylate.

D-9. Ethyl 8-ethyl-5,8-dihydro-4-methyl-5-oxo-2-(4-pyridinyl)pyrido[2,3-d]pyrimidine-6-carboxylate using ethyl 5,8-dihydro-4-methyl-5-oxo-2-(4-pyridinyl)pyrido[2,3-d]pyrimidine-6-carboxylate.

Following the procedure in Example D-1 but using in place of ethyl iodide a corresponding molar equivalent quantity of the appropriate lower-alkyl salt, the compounds of Examples D-10 through D-13 are obtained:

d-10. Ethyl 5,8-dihydro-8-methyl-5-oxo-2-(4-pyridinyl)pyrido[2,3-d]pyrimidine-6-carboxylate using dimethyl sulfate.

D-11. Ethyl 5,8-dihydro-5-oxo-8n-propyl-2-(4-pyridinyl)pyrido[2,3-d]pyrimidine-6-carboxylate using n-propyl iodide.

D-12. Ethyl 5,8-dihydro-8-isobutyl-5-oxo-2-(4-pyridinyl)pyrido[2,3-d]pyrimidine-6-carboxylate using isobutyl bromide.

D-13. Ethyl 8-n-hexyl-5,8-dihydro-5-oxo-2-(4-pyridinyl)pyrido[2,3-d]pyrimidine-6-carboxylate using n-hexyl chloride.

Following the procedure described in Example D-2 but using in place of ethyl 8-ethyl-5,8-dihydro-5-oxo-2-(4-pyridinyl)pyrido[2,3-d]pyrimidine-6-carboxylate a molar equivalent quantity of the appropriate lower-alkyl 5,8-dihydro-8-(lower-alkyl)-5-oxo-2-Q-pyrido[2,3-pyrimidine-6-carboxylate, the compounds of Examples D-14 through D-24 are obtained:

D-14. 8-Ethyl-5,8-dihydro-2-(2-methyl-4-pyridinyl)-5-oxopyrido[2,3-d]pyrimidine-6-carboxylic acid using ethyl 8-ethyl-5,8-dihydro-2-(2-methyl-4pyridinyl)-5-oxopyrido[2,3-d]pyrimidine-6-carboxylate.

D-15. 8-Ethyl-5,8-dihydro-2-(3-methyl-4-pyridinyl)-5-oxopyrido[2,3-d]pyrimidine-6-carboxylic acid using ethyl 8-ethyl-5,8-dihydro-2-(3-methyl-4-pyridinyl)-5-oxopyrido[2,3-d]pyrimidine-6-carboxylate.

D-16. 8-Ethyl-2-(2-ethyl-4-pyridinyl)-5,8-dihydro-5-oxopyrido[2,3-d]pyrimidine-6-carboxylic acid using ethyl 8-ethyl-2-(2-ethyl-4-pyridinyl)-5,8-dihydro-5-oxopyrido[2,3-d]pyridimine-6-carboxylate.

D-17. 8-Ethyl-5,8-dihydro-2-(2,6-dimethyl-4-pyridinyl)-5-oxypyrido[2,3-d]pyrimidine-6-carboxylic acid using ethyl 8-ethyl-5,8-dihydro-2-(2,6-dimethyl-4-pyridinyl)-5-oxopyrido[2,3-d]pyrimidine-6-carboxylate.

D-18. 8-Ethyl-5,8-dihydro-4-methyl-5-oxo-2-(4-pyrido[2,3-d]pyrimidine-6-carboxylic acid using ethyl 8-ethyl-5,8-dihydro-4-methyl-5-oxo-2-(4-pyridinyl)-pyrido[2,3-d]pyrimidine-6-carboxylate.

D-19. 5,8-Dihydro-8-methyl-5-oxo-2-(4-pyridinyl)-pyrido[2,3-d]-pyrimidine-6-carboxylic acid using methyl 5,8-dihydro-8methyl-5-oxo-2-(4-(pyridinyl)-pyrido[2,3-d]-pyrimidine-6-carboxylate.

D-20. 5,8-Dihydro-5-oxo-8-n-propyl-2-(4-pyridinyl)-pyrido[2,3-d]pyrimidine-6-carboxylic acid using n-propyl 5,8-dihydro-5-oxo-8-n-propyl-2-(4-pyridinyl)-pyrido[2,3-d]pyrimidine-6-carboxylate.

D-21. 5,8-Dihydro-8-isobutyl-5-oxok-2-(4-pyridinyl)pyrido[2,3-d]pyrimidine-6-carboxylic acid using isobutyl 5,8-dihydro-8-isobutyl-5-oxo-2-(4-pyridinyl)pyrido[2,3-d]pyrimidine-6-carboxylate.

D-22. 8n-Hexyl-5,8-dihydro-5-oxo-2-(4-pyridinyl)-pyrido[2,3-d]pyrimidine-6-carboxylic acid using n-hexyl 8-n-hexyl-5,8-dihydro-5-oxo-2-(4-pyridinyl)-pyrido[2,3-d]-pyrimidine-6-carboxylate.

D-23. 8-Ethyl-5,8-dihydro-5-oxo-4-n-propyl-2-(4-pyridinyl)pyrido[2,3-d]pyrimidine-6carboxylic acid is obtained by following the respective procedures of Examples D-1 and D-2 starting with a corresponding molar equivalent quantity of ethyl 5,8-dihydro-5-oxo-4-n-propyl-2-(4-pyridinyl)pyrido[2,3-d]pyrimidine-6-carboxylate in place of ethyl 5,8-dihydro-5-oxo-2-(4-pyridinyl)pyrido[2,3-d]pyrimidine-6-carboxylate to obtain ethyl 8-ethyl-5,8-dihydro-5-oxo-4-n-propyl-2-(4-pyridinyl)pyrido[2,3-d]pyrimidine-6-carboxylate and hydrolyzing this ester as in Example D-2 to produce 8-ethyl-5,8-dihydro-5-oxo-4-n-propyl-2-(4-pyridinyl)pyrido[2,3-d[pyrimidine-6-carboxylic acid.

The actual determination of the numerical anti-bacterial data definitive for a particular compound of the invention is readily obtained by known standard test procedures by technicians versed in antibacterial test procedures, without need for any extensive experimentation.

The compounds of the invention can be prepared for use by conventional pharmaceutical procedures: that is, by dissolving or suspending them in a pharmaceutically acceptable vehicle, e.g., aqueous alcohol, glycol, oil solution, or oil-water emulsion, for parenteral or oral administration; or by incorporating them in unit dosage form as tablets or capsules for oral administration either alone or in combination with convention adjuvants, e.g., calcium carbonate, starch, lactose, talc, magnesium stearate, gum acacia, and the like.

We claim:

1. 4-$R_2$-5,8-dihydro-8-(lower-alkyl)-5-oxo-2-Q-6-Z-pyrido[2,3-d]pyrimidine having the formula

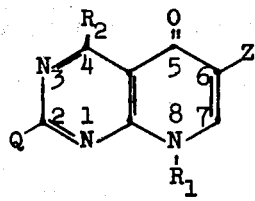

where $R_1$ is lower-alkyl, Z is carboxy or lower-carbalkoxy, $R_2$ is hydrogen or lower-alkyl and Q is 4(or 3)-pyridinyl or 4(or 3)-pyridinyl having one or two lower-alkyl substituents.

2. A compound according to claim 1 where Z is carboxy.

3. A compound according to claim 2 where $R_2$ is hydrogen.

4. 8-Ethyl-5,8-dihydro-5-oxo-2-(4-pyridinyl)-pyrido[2,3-d]pyrimidine-6-carboxylic acid according to claim 3.

5. 8-Ethyl-5,8-dihydro-5-oxo-2-(3-pyridinyl)-pyrido[2,3-d]pyrimidine-6-carboxylic acid according to claim 3.

6. 4-$R_2$-5,8-dihydro-5-oxo-2-Q-6-Z-pyrido[2,3-d]-pyrimidine having the formula

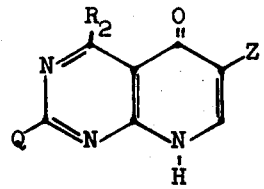

or its tautomeric 4-$R_2$-5-hydroxy-2-Q-6-Z-pyrido[2,3-d]pyrimidine, where Z is carboxy or lower-carbalkoxy, $R_2$ is hydrogen or lower-alkyl and Q is 4(or 3)-pyridinyl or 4(or 3)-pyridinyl havine one or two lower-alkyl substituents.

7. A compound according to claim 6 where Z is lower-carbalkoxy.

8. A compound according to claim 7 where $R_2$ is hydrogen.

9. Ethyl 5,8-dihydro-5-oxo-2-(4-pyridinyl)-pyrido[2,3-d]pyrimidine-6-carboxylate or its tautomeric ethyl 5-hydroxy-2-(4-pyridinyl)pyrido[2,6-d]pyrimidine-3-carboxylate according to claim 8.

10. Ethyl 5,8-dihydro-5-oxo-2-(3-pyridinyl)-pyrido[2,3-d]pyrimidine-6-carboxylate or its tautomeric ethyl 5-hydroxy-2-(3-pyridinyl)pyrido[2,3-d]pyrimidine-6-carboxylate according to claim 8.

* * * * *

UNITED STATES PATENT AND TRADEMARK OFFICE
CERTIFICATE OF CORRECTION

PATENT NO. : 3,992,380
DATED : November 16, 1976
INVENTOR(S) : George Y. Lesher and Baldev Singh It is certified that error appears in the above-identified patent and that said Letters Patent are hereby corrected as shown below:

Column 1, line 35, following "formula" omit "10/10".

Column 2, line 46, "product" should read -- produce --.

Column 2, line 48, "product" should read -- produce --.

Column 3, line 5, "R is ethyl" should read -- $R_1$ is ethyl --.

Column 3, line 43, "product" should read -- produce --.

Column 3, line 45, "product" should read -- produce --.

Column 4, line 4, "'pyridinyl'," second occurrence, should read -- "pyridyl" --.

Column 4, line 42, between "boxylic" and "cationic" insert -- acid --.

Column 5, line 39, "correspondance" should read -- correspondence --.

Column 6, line 36, "4hy-" should read -- 4-hy- --.

Column 6, line 38, "product" should read -- produce --.

Column 6, line 41, between "known" and "compounds" omit "as".

UNITED STATES PATENT AND TRADEMARK OFFICE
CERTIFICATE OF CORRECTION

PATENT NO. : 3,992,380
DATED : November 16, 1976
INVENTOR(S) : George Y. Lesher and Baldev Singh It is certified that error appears in the above-identified patent and that said Letters Patent are hereby corrected as shown below:

Column 16, Claim 9, line 45, "[2,6-" should read -- [2,3- --; and, line 46, "3-carboxylate" should read -- 6-carboxylate --.

Column 16, Claim 6, line 37, "havine" should read -- having --.

Signed and Sealed this

Twenty-ninth Day of March 1977

[SEAL]

Attest:

RUTH C. MASON
*Attesting Officer*

C. MARSHALL DANN
*Commissioner of Patents and Trademarks*